United States Patent [19]

Capone

[11] 4,135,382

[45] Jan. 23, 1979

[54] APPARATUS FOR DEVELOPING A COUNTERFLOW TO CLEAN A FLUID CONVEYING CONDUIT OF A GAS ANALYZER

[75] Inventor: David M. Capone, Oakmont, Pa.

[73] Assignee: Thermo-Lab Instruments, Inc., Pittsburgh, Pa.

[21] Appl. No.: 871,489

[22] Filed: Jan. 23, 1978

[51] Int. Cl.² .................. G05D 9/00; G01N 27/00
[52] U.S. Cl. ........................... 73/23; 137/102; 204/195 R; 204/195 S; 422/83; 422/119
[58] Field of Search .............. 137/102; 204/195 S, 204/195 R, 1 S; 73/23; 23/232 R, 254 R

[56] References Cited

U.S. PATENT DOCUMENTS

| | | | |
|---|---|---|---|
| 3,357,232 | 12/1967 | Lauer | 73/23 |
| 3,516,443 | 6/1970 | Hughes | 137/102 X |

Primary Examiner—G. L. Kaplan
Attorney, Agent, or Firm—Stanley J. Price, Jr.; John M. Adams

[57] ABSTRACT

An eductive flow loop has an inlet leg conduit projecting into an exhaust stack and an outlet leg conduit. A sample of gaseous combustion by-products is withdrawn from the exhaust stack into the inlet leg conduit and flows to the outlet leg conduit. A portion of the sample is drawn through a convective flow loop conduit and a gas sensing device and back to the outlet leg conduit and therefrom back into the exhaust stack. A counterflow device is positioned in the outlet leg conduit between the exhaust stack and the convective flow loop conduit. The counterflow device includes a portion of the outlet leg conduit that communicates with the exhaust stack and a blowback conduit connected to the outlet leg conduit. A stop member is movably positioned in the blowback conduit. When the fluid pressure in the blowback conduit is greater than the pressure of the gas sample flow, the stop member moves into the outlet leg conduit to block flow to the exhaust stack. Fluid flow is thus directed from the blowback conduit through the outlet leg conduit in a direction opposite to the normal direction of flow of the gas sample through the eductive and convective flow loop conduits. The counterflow of fluid dislodges particulate matter that builds up on the inner wall of the loop conduits when wet and dirty gas is sampled by the gas analyzer and/or prevents an explosive mixture of gases from entering the gas analyzer.

10 Claims, 3 Drawing Figures

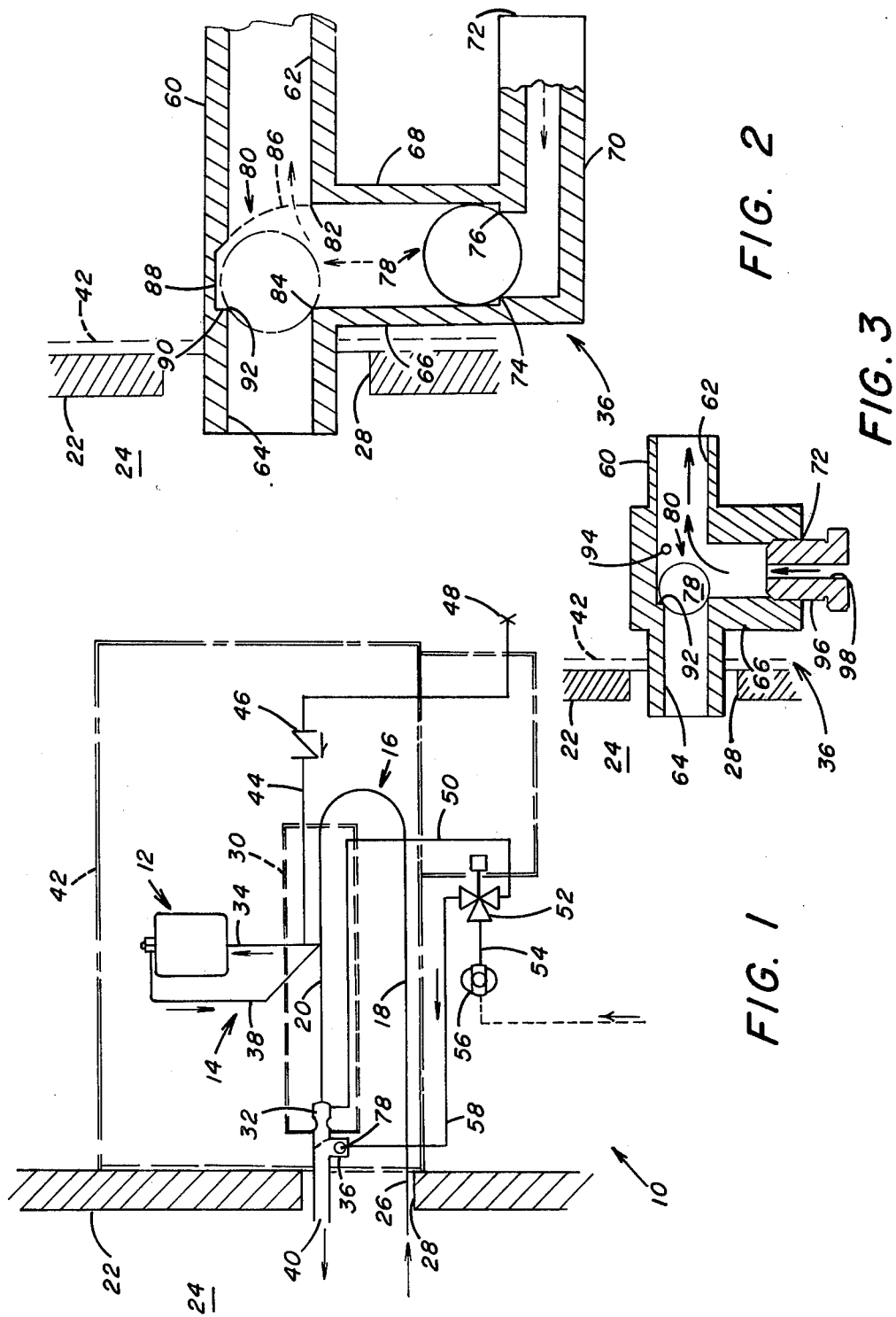

APPARATUS FOR DEVELOPING A COUNTERFLOW TO CLEAN A FLUID CONVEYING CONDUIT OF A GAS ANALYZER

BACKGROUND OF THE INVENTION

1. Field of the Invention

This invention relates to apparatus for removing particulate deposits that collect on the inner wall of a conduit that conveys wet and dirty gas and the like, and more particularly to a blowback device for developing a fluid counterflow in a conduit that conveys gaseous products of combustion from a combustion process to a gas analyzer for the purpose of cleaning the inner wall of the conduit and/or preventing an explosive mixture of combustible material from entering the gas analyzer.

2. Description of the Prior Art

A gas analyzer of the type disclosed in U.S. Patent application Ser. No. 739,712, entitled "Method And Apparatus For Conveying A Gas Sample Through An Analyzer Chamber" filed Nov. 8, 1976, includes a pair of gas sample flow loops that are connected to each other and are operable to convey a sample of combustion product gas from a combustion process to a gas analyzer for the purpose of measuring the combustibles and oxygen concentration in the gaseous sample. An eductive loop has an inlet portion that collects a sample of the combustion product gas from the combustion process and conveys the sample to an outlet. With this arrangement, a sample of the combustion product gas is withdrawn from the combustion process for analysis. A convective loop is connected in fluid communication with the eductive loop at a point upstream from an aspirator, which is located adjacent to the outlet of the eductive loop and is operable to maintain circulation of the gas sample through the eductive and convective loops. A gas sensor of the type manufactured and sold by Thermox Instruments, Inc. of Pittsburgh, Pa., is positioned in the convective loop and is operable to analyze a sample of the gas taken from the eductive loop to make a determination of net excess oxygen or net excess combustibles in the gas sample.

When a dirty gas having particulate matter entrained therein is sampled, the particulate matter builds up after a period of time on the inner walls of the loop conduits. If this condition is allowed to continue in the sampling of a dirty gas, the conduits will eventually become clogged limiting or terminating flow entirely to the gas analyzer. Consequently, the gas sensor ceases to function at full efficiency. Furthermore, the presence of an explosive mixture of combustible material in the conduits of the gas analyzer presents a hazard of an explosion occurring in the gas analyzer which operates at elevated temperatures. This condition could occur, for example, in the event the flame of a combustion process fails, thereby permitting an explosive mixture of gas and air to enter the conduits of the gas analyzer.

To avert plugging of the conduits by the buildup of particulate matter on the conduit walls and to clean the conduits, blowback devices have been utilized as disclosed in the above mentioned patent application to develop a flow of air through the eductive and convective loops to dislodge particulate matter from the inner walls of the loop conduits and flush the matter from the conduits. It is the conventional practice in the backblowing of a fluid conveying conduit to utilize a conventional rotary valve which when rotated in a preselected direction discontinues flow of the gas sample through the eductive loop and permits air under pressure to enter the eductive loop and flow in a direction opposite to the flow of the gas sample. In this manner, the eductive loop is flushed of built-up deposits and unrestricted flow of the gas sample to the gas analyzer is maintained.

Conventional valves utilized in backblowing contain seals, which after prolonged use of the valve are subject to leakage and malfunction when exposed to a gas sample at an elevated temperature. In addition, mechanical valves must be positioned in a location which accommodates the size of the valve and permits access for actuation. For large valves this presents a problem because the loop conduit must be structured to provide access to the valve. Frequently, the limitations placed on the location of the blowback valve interferes with the operation of the gas analyzer. Also, during normal operation of the gas analyzer when the gas sample flows through the loop conduits, mechanical blowback valves have a tendency to restrict the gas flow through the loop conduits.

There is need for an apparatus to develop a counterflow in a conduit conveying a fluid with particulate matter entrained therein to remove deposits of the particulate matter from the inner wall of the conduit. The counterflow apparatus must be easily adapted to a preselected conduit structure associated with a gas analyzer. The counterflow apparatus must further provide unrestrictive flow of a gas sample through the conduit when counter flow is not required and be operable to prevent leakage of the gas sample during counterflow operations and withstand the elevated temperatures of the gas sample.

SUMMARY OF THE INVENTION

In accordance with the present invention there is provided in a gas analyzer apparatus for developing fluid counterflow in a fluid conveying conduit to remove deposits from the inner wall of the conduit and to prevent the entrance of an explosive mixture of combustible material into the gas analyzer in which the apparatus includes a first conduit for conveying a sample fluid in a first direction. The first conduit has an inlet and an outlet. A second conduit is connected to the first conduit between the inlet and the outlet of the first conduit and is operable to convey a counterflow fluid to the first conduit. The first conduit has a valve seat positioned oppositely of the outlet of the second conduit. A stop mechanism is movably supported in the second conduit and is operable to control fluid flow from the second conduit to the first conduit. The stop mechanism is normally maintained in the second conduit displaced from the first conduit to permit flow of the sample fluid through the first conduit in the first direction from the inlet to the outlet of the first conduit. The stop mechanism upon actuation is operable upon flow of the counter-fluid through the second conduit to move from the second conduit to the first conduit into sealing relation with the valve seat to block flow from the inlet to the outlet of the first conduit and direct flow from the second conduit to the first conduit and through the first conduit in a direction opposite to the flow of the sample fluid in the first direction of flow through the first conduit.

A seat is provided within the second conduit for supporting the stop mechanism in the second conduit to permit flow of the fluid sample through the first conduit in the first direction. The second conduit includes an inlet and an outlet with the outlet communicating with the first conduit between the inlet and outlet of the first conduit. The stop mechanism is operable to move from the second conduit outlet into sealing relation with a shoulder portion which forms the valve seat of the first conduit when the fluid pressure exerted upon the stop mechanism by the fluid flow through the second conduit is sufficient to move the stop mechanism from the second conduit to the first conduit. The stop mechanism is retained in sealing relation with the shoulder by fluid flow from the second conduit into the first conduit. With the outlet to the first conduit being blocked by the stop mechanism, the fluid flow is directed by the stop mechanism toward the inlet of the first conduit. In this manner a counterflow of fluid is established through the first conduit in a direction opposite to the normal direction of flow of the sample fluid, such as a flue gas, through the first conduit. The fluid counterflow is operable to remove built-up particles that have collected on the walls of the first conduit, as well as on the walls of the conduits of the gas analyzer. Also, the counterflow is effective to prevent the entrance of an explosive mixture of material, such as an explosive mixture of gases from entering the conduits of the gas analyzer.

A guide, such as a grooved portion or a pin, is positioned in the first conduit. The grooved portion extends from the outlet of the second conduit to the shoulder portion of the first conduit. The grooved portion guides the movement of the stop mechanism from the second conduit to the first conduit and into sealing relation with the shoulder portion when the fluid pressure on the stop mechanism is sufficient to move the stop mechanism from the second conduit to the first conduit. With a pin, the stop mechanism is deflected toward the shoulder portion of the first conduit. The stop mechanism, which is preferably a ball-shaped member, when maintained in sealing relation with the shoulder portion blocks flow through the first conduit to the outlet thereof. With the ball-shaped member engaging the shoulder portion, fluid flow is directed from the second conduit and through the first conduit in a direction opposite to the normal direction of flow of the fluid sample through the first conduit.

Preferably, the counterflow apparatus is associated with a loop conduit having an inlet leg in fluid communication with an exhaust stack or chamber containing a gas to be analyzed and an outlet leg communicating with the exhaust stack. The counterflow apparatus is positioned in the outlet leg downstream of an air-operated aspirator which is connected to the outlet leg. A gas analyzer is connected to the loop conduit between the inlet and outlet legs. The gas sample from the analyzer is drawn through the aspirator and conveyed through the counterflow apparatus to the exhaust stack. The gas analyzer is preferably an electrochemical cell that is operable to measure the oxygen partial pressure of a flue gas. The gas analyzer receives a portion of the sample of the flue gas that is extracted from the exhaust stack that extends from a combustion process. The gas sample is drawn into the inlet leg of the loop conduit. The gas sample under normal operations is exhausted to the outlet leg and through the counterflow device back into the exhaust stack.

The ball-shaped member of the counterflow device is normally maintained in contact with a seat in a blowback conduit communicating with the outlet leg. Upon initiation of fluid flow through the blowback conduit, the ball-shaped member is moved into sealing relation with a valve seat provided in the outlet leg of the loop conduit to establish a backflow or counterflow through the outlet leg and the inlet leg of the loop conduit. In this manner, particulate matter build-up on the inner walls of the loop conduit is dislodged and flushed from the loop conduit to prevent plugging of the system. In addition, the counterflow operation can be utilized to prevent the entrance of an explosive mixture of combustible material into the conduits of the gas analyzer.

Accordingly, the principal object of the present invention is to provide apparatus for developing counterflow in a fluid conveying conduit to remove deposits from the inner wall of the conduit and/or to prevent the entrance of an explosive mixture of combustible material into the conduits of a gas analyzer.

Another object of the present invention is to provide an apparatus for backblowing a looped conduit that conveys a gas sample from a combustion process to a gas analyzer for analyzing the condition of the gas sample where the apparatus effects fluid flow in a direction opposite to the direction of flow of the gas sample through the looped conduit for flushing from the loop conduit built-up deposits.

Another object of the present invention is to provide an apparatus for purging the conduits of a gas analyzer to prevent the entrance of an explosive mixture of gases into the gas analyzer.

These and other objects of the present invention will be more completely disclosed and described in the following specification, the accompanying drawings and the appended claims.

BRIEF DESCRIPTION OF THE DRAWINGS

FIG. 1 is a schematic representation of a gas sensor that includes a loop conduit that conveys a sample of the combustion product gases from a combustion process to and from a gas analyzer, illustrating a counterflow apparatus at the outlet of the loop conduit for developing a backflow to dislodge built-up deposits from the inner wall of the conduit.

FIG. 2 is an enlarged schematic representation of the counterflow apparatus; illustrating a ball-shaped stop member seated in a first position to permit flow of the gas sample through the loop conduit and in a second position, shown in phantom, to permit backflow of fluid through the loop conduit in a direction opposite to the normal direction of flow of the gas sample through the loop conduit.

FIG. 3 is a schematic representation similar to FIG. 2, illustrating another embodiment of the counterflow apparatus.

DESCRIPTION OF THE PREFERRED EMBODIMENT

Referring to FIG. 1 of the drawings, there is illustrated a gas analyzer generally designated by the numeral 10 for measuring the net excess oxygen or combustibles in the gaseous by-products of a combustion process and/or the total combustibles and the total oxygen in the gaseous by-products. The gas analyzer 10 includes a heated gas sensing device generally designated by the numeral 12 that is preferably enclosed in a heated cabinet 42 and is connected by a convective flow loop conduit 14 to an eductive flow loop conduit 16. The eductive flow loop conduit 16 is a continuous conduit having an inlet leg 18 containing a 180° bend and an outlet leg 20 connected thereto. In accordance with the present invention, the inlet leg 18 is attached in a conventional manner in fluid flow communication with combustion chamber apparatus, such as a housing or sidewall 22 of an exhaust stack 24 or a flue gas conduit, duct, or the like through which the gaseous by-products of a combustion process are conveyed. For the purpose of illustration in the present invention, the gas analyzer 10 is associated with an exhaust stack of a combustion process.

An inlet 26 of the eductive loop inlet leg 18 protrudes through an opening 28 in the sidewall 22 of the exhaust stack 24 for withdrawing a sample of the gaseous by-products from the exhaust stack. The sample flows through the inlet leg 18 and around the bend to the outlet leg 20. The inlet leg 18 extends to a heated flow block 30 and is connected to the convective flow loop conduit 14 within the flow block. The outlet leg 20 extends through the flow block 30 and includes downstream an aspirator 32. The aspirator 32 creates suction within the eductive flow loop conduit 16 and consequently a sample of the gas is drawn from the exhaust stack 24 into the inlet 26 to the inlet leg 18.

As the gas sample flows through the eductive flow loop conduit 16, a portion of the sample flows by thermal convection into an inlet leg 34 of the convective flow loop conduit 14. The inlet leg 34 and outleg leg 38 of the convective flow loop communicate with the connection of the inlet leg 18 and outlet leg 20 in the flow block 30. With this arrangement the inlet leg 18 terminates and the outlet leg 20 begins at the intersection of legs 34 and 38 in flow block 30. At a point downstream of the aspirator 32, the aspirator is connected in fluid communication with a device generally designated by the numeral 36 for developing a counterflow in the eductive flow loop conduit 16 to remove deposits collected on the inner walls of the inlet and outlet legs 18 and 20 in accordance with the present invention. The counterflow device 36 is illustrated in greater detail in FIGS. 2 and 3.

When the counterflow device 36 is not in operation, the gas sample drawn from the exhaust stack 24 is conveyed from the loop conduit 16 into the inlet leg 34 of the convective flow loop conduit 14 and through the gas sensing device 12. The gas sensing device 12 preferably includes a ceramic oxygen electrochemical cell that operates at elevated temperatures and measures the oxygen partial pressures of the gas sample. Suitable electrochemical cells for measuring oxygen partial pressures are well known in the art and suitable cells for use in the present invention are disclosed in U.S. Pat. Nos. 3,597,345; 3,865,707 and 3,869,370 which are incorporated herein by reference.

As disclosed in the above-mentioned patents a portion of the gas sample flows by thermal convection past the sensing device 12. The oxygen partial pressure is recorded and indicated by an electrical signal which is converted to a direct reading of the excess oxygen or excess fuel contained in the gas sample. The sensed portion of the sample is then conveyed to the outlet leg 20 via outlet leg 38 of the convective flow loop conduit 14. The aspirator 32 is operable to draw the fluid through the outlet leg 20 and the counterflow device 36 to an outlet 40 of the eductive flow loop conduit 16. The outlet 40 extends through the sidewall 22 into the exhaust stack 24. With this arrangement the gas sample is returned to the exhaust stack 24.

Preferably, though not necessarily, the inlet and outlet legs 18 and 20 have their openings in stack 24 at a location of the same, or approximately the same, stack pressure. Consequently, the rate of flow of gas sample through the eductive flow loop conduit 16 is unaffected, or substantially unaffected, by fluctuations in the stack pressure. Thus, the desired rate of flow having been initially set by establishing the operating parameters of the aspirator 32, the analyzer 10 will provide substantially continuous analysis of the gas sample at substantially the same flow rate without requiring readjustment due to variations in the stack pressure.

As further illustrated in FIG. 1, the eductive flow loop conduit 16, as well as the convective flow loop conduit 14 and the gas sensing device 12, are housed within a casing 42 that may be bolted to a mounting plate that is, in turn, attached to the external surface of sidewall 22 in front of the opening 28. The inlet leg 34 of the convective flow loop conduit 14 is connected within flow block 30 to a conduit 44 that extends from the casing 42 through a check valve 46 to a calibration port 48. The calibration port 48 is plugged when not calibrating the gas sensing device 12 and during calibration of device 12 fluid to the aspirator 32 is terminated. The aspirator 32 is connected by a conduit 50 that extends from the casing 42 to one outlet of a solenoid valve 52 which is, in turn, connected at the inlet to the valve 52 by a conduit 54. The conduit 54 is connected through an air regulator 56 to a source (not shown) of pressurized fluid. The solenoid valve 52 is also connected through a second outlet to a conduit 58 that extends into the casing 42 and is connected to the inlet of the counterflow device 36. With this arrangement the solenoid valve 52 controls operation of the counterflow device 36 for the blowback operations and the aspirator 32 for gas analysis operations.

During operation of the gas analyzer 10 the flow of a gas sample is developed through the convective flow loop conduit 14 and eductive flow loop conduit 16 by the aspirator 32. During periods in which fluid counterflow is developed through the eductive flow loop conduit 16, solenoid valve 52 terminates the motive fluid flow to the aspirator 32 and flow of the gas sample from the inlet leg 18 to the outlet leg 20. The solenoid valve 52 also conveys fluid under pressure from the source through the conduit 58 to the counter flow device 36. The counter flow device 36 then directs fluid flow through the outlet leg 20 in a direction opposite to the flow of the gas sample through the leg 20. In accordance with one feature of the present invention, the counterflow of fluid dislodges built-up particulate matter from the inner walls of the inlet and outlet legs 34 and 38 and removes the matter from the loop conduit 16. The blowback operation is conducted periodically to prevent plugging of the eductive flow loop conduit 16. Further, in accordance with the present invention, the blowback operation is also conducted to purge the plumbing of the gas sensing device 12 when an explosive mixture of combustible material is flowing through the stack 24. Thus the blowback operation is operable to prevent the entrance of an explosive mixture of gases from the stack 24 into the device 12 and the possible occurrence of an explosion in the device 12.

As illustrated in FIG. 2, the counterflow device 36 includes a first conduit 60 having an inlet portion 62 that is connected to the outlet of the aspirator 32 illustrated in FIG. 1. An outlet portion 64 of first conduit 60 corresponds to the outlet 40 or exhaust of FIG. 1 for the eductive flow loop conduit 16 to the stack 24. The outlet portion 64 extends through an opening of the casing 42 to exhaust the gas sample back into the exhaust stack 24. A second conduit 66 is connected to the first conduit 60 and includes an outlet portion 68 that extends substantially perpendicular to the conduit 60 and a second portion 70. The second portion 70 includes an inlet 72 arranged in fluid communication with the conduit 58 extending from the solenoid valve 52 illustrated in FIG. 1. With this arrangement pressurized fluid is directed through conduit 58 into the inlet 72 of the counterflow device 36. A shoulder 74 extends inwardly from the inner wall of the conduit portion 68 to form a valve seat 76 for receiving a stop member generally designated by the numeral 78. Preferably, the stop member has a spherical configuration, such as a ball shape in which the diameter of the ball is greater than the diameter of the conduit portion 68 at the shoulder 74. When a gas sample is being analyzed the stop member 78 remains closely adjacent to the seat 76.

Conduit 66 is arranged in fluid communication with conduit 60 between the inlet 62 and the outlet 64 at conduit shoulder 82. A guide portion generally designated by the numeral 80 is formed in the inner wall of the conduit 60 and includes a groove 86 which extends from the outlet 68 of conduit 66 along an arcuate or curved path toward the outlet 64 of conduit 60 and forms a recess 88 in conduit 60. The recess 88 terminates in a shoulder 90 that forms with opposite shoulder 84 a valve seat 92 located between the inlet 62 and the outlet 64 of conduit 50. Seat 92 is arranged to receive the stop member 78 in a position to seal the outlet 64 from the inlet 62 and to direct fluid flow from the conduit 66 to the conduit 60 and the aspirator 32 and through the outlet leg 20 in a direction opposite to the normal direction of flow of the gas sample through the outlet leg 20 and conduit 60.

Upon termination of the flow of the gas sample through the eductive flow loop conduit 16 and the introduction of blowback air into the inlet 72 of the conduit portion 70, the differential pressure acting upon the stop member 78 is sufficient to move the stop member from seat 76 to seat 92. The counterfluid is conducted at a sufficiently high pressure to dislodge particulate matter from the inner walls of the loop conduit 14 and flush the matter out of the conduit through inlet 26. In addition, as stated herein above, blowback of air through the loop conduit 16 is operable to prevent the entrance of an explosive mixture of combustible material into the gas sensing device 12.

The diameter of the stop member 78 is greater than the diameter of the valve seat 92 formed by shoulders 84 and 90. Therefore, when the stop member 78 engages the valve seat 92 the conduit 60 is sealed at the valve seat 92. Fluid flow from conduit 66 is deflected by the stop member 78 into the conduit 60 toward the inlet 62. The stop member 78 is moved into contact with the valve seat 92 by fluid flow from conduit 66. The stop member 78 is maintained in sealing relation with valve seat 92 when the fluid pressure through conduit 66 extends the fluid pressure through conduit 60.

Cleaning the conduit loops 14 and 16 and the gas sensing device 12 by the counterflow device 36 eliminates the problems encountered heretobefore with conventional mechanically actuated valves for introducing blowback air into the system. The counterflow device 36 of the present invention provides blowback operations which do not restrict the flow of the gas sample through the gas analyzer 10 and are not affected by elevated temperatures of the gas sample. Furthermore, the device 36 does not include seals and the problems associated therewith are thus avoided.

In operation when blowback air is desired to be conducted through the conduit loops 14 and 16 and the gas sensing device 12, the solenoid valve 52 located at a position remote from the casing 42 is actuated to terminate operation of the aspirator 32. With the aspirator 32 deactivated, flow of the gas sample into the inlet 26 and through the inlet and outlet legs 18 and 20 is terminated. Coincident with termination of operation of aspirator 32 is the actuation of the counterflow device 36 by the conveyance of fluid under pressure from the source through the regulator 56 and conduit 54 to the solenoid valve 52. The solenoid valve 52 directs the fluid under pressure through the conduit 58 and into the inlet 72 of the counterflow device 36. As stated hereinabove the fluid pressure exerted upon the stop member 78 by fluid flow into inlet 72 is sufficient to displace the stop member from its initial position on valve seat 76 to its operative position on valve seat 92, as illustrated in phantom in FIG. 2.

When a gas sample is being analyzed, a continuous stream of sample gas flows through the exhaust stack 24 through the eductive flow loop conduit 16 and passes through conduit 60 of the counterflow device 36 to the outlet 40 and back into the exhaust stack 24. During this operation the sample gas flow is not obstructed by the stop member 78. Generally the gas sample being analyzed is corrosive in nature. Therefore, in order to prevent the corrosive gas from contacting the stop member 78 a slight flow is established by providing a by-pass around solenoid valve 52 or by providing limited flow through solenoid valve 52 to the conduit 58 to prevent the sample gas from entering conduit 66. The force of the flow is insufficient, however, to move the stop member 78 out of the conduit 66.

More specifically, the flow is sufficient only to raise the stop member 78 from the seat 76 and permit flow into the conduit portion 68. In this case the flow is only of sufficient magnitude to raise the stop member 78 from the seat 76 while maintaining the stop member within the conduit portion 68. The flow enters the conduit 60 and prevents flow of the gas sample into the conduit portion 68 and into contact with the stop member 78. Thus, the stop member 78 is protected from the deleterious effects of a corrosive by-product combustion gas. Also, this practice serves to prevent the member 78 from sticking to the seat 76. To return the stop member 78 to the seat 76, or closely adjacent thereto, the fluid flow to inlet 72 is terminated, or substantially reduced.

Referring to FIG. 3, there is illustrated another embodiment of the counterflow device 36 in which the groove 86 is substituted by a pin 94 or like means to direct the stop member 78 to move into sealing contact with the valve seat 92 and prevent the member 78 from moving into inlet portion 62 of conduit 60 during the blowback operation. Preferably, the pin 94 is secured to the inner wall of conduit 60 and extends perpendicular to the inner wall opposite the outlet of conduit 66. In this position the pin 94 prevents the member 78 from moving into the inlet portion 62 and directs the member 78 to move from the end of an adapter 96 secured to inlet 72 of conduit 66 to the valve seat 92.

The adapter 96 has an axial passageway 98 that opens into conduit 66 to permit blowback fluid to enter conduit 66 from passageway 98. The passageway 98 is arranged in fluid communication with the conduit 58, illustrated in FIG. 1, extending from the solenoid valve 52. During analysis of the gas sample the stop member 78 is retained within conduit 66 and the sample flows from inlet 62 to outlet 64. As stated above, sufficient backflow may be provided to prevent the corrosive gas sample from entering conduit 66 from conduit 60.

As illustrated in FIG. 3, the flow of blowback fluid through conduit 66 moves the member 78 into conduit 60, and the pin 94 directs the member 78 toward the valve seat 92. The fluid flow from conduit 66 maintains the member 78 in sealing relation with valve seat 92. With the member 78 engaging seat 92, the fluid from conduit 66 is directed toward inlet portion 62 of conduit 60 in a direction opposite to the normal direction of flow of the sample fluid through conduit 60. Blowback fluid may also be introduced into inlet portion 62 while the gaseous sample is being analyzed. In this case the flow of blowback fluid opposes the flow of the gaseous sample. However, flow through the loop conduit 16 must be terminated, as well as the blowback flow, in order to allow the member 78 to drop down into the conduit 66.

As above discussed the counterflow device 36 is operable to prevent the entrance of an explosive mixture of combustible material into the conduit of the gas sensing device 12 and the consequences of a resultant explosion. Such a hazard is presented, for example, by the failure of an igniting device. In this case an explosive mixture of fuel gas and air would flow through the exhaust stack 24 and would be free to enter the loop conduit 16 and the gas sensing device 12. The explosive mixture would be ignited by the elevated temperature of the device 12. However, with the present invention the counterflow device 36 is operable to direct a counterflow of noncombustible fluid through the device 12 and loop conduit 16 to prevent the entrance of an explosive mixture thereof. To this end suitable control means responsive to the failure or absence of the flame in the combustion process would be operable to initiate the counterflow operation by actuating the solenoid valve 52. Actuation of valve 52 conveys the counterflow fluid to the counterflow device 36 and terminates operation of aspirator 32 as above discussed. In this manner a counterflow is developed through the loop conduits 14 and 16 to prevent entrance of an explosive mixture of combustible material flowing through the stack 24 from entering the loop conduits 14 and 16.

According to the provisions of the Patent Statutes, I have explained the principle, preferred construction and mode of operation of my invention and have illustrated and described what I now consider to represent its best embodiments. However, it should be understood that, within the scope of the appended claims, the invention may be practiced otherwise than as specifically illustrated and described.

I claim:

1. In a gas analyzer, apparatus for developing a counterflow in a fluid conveying conduit to remove deposits from the inner wall of the conduit and to prevent the entrance of an explosive mixture of combustible material into the gas analyzer comprising, a first conduit having an inlet and an outlet, said first conduit being operable to convey fluid in a first direction from said inlet to said outlet, a second conduit connected to said first conduit between said inlet and said outlet of said first conduit for conveying fluid to said first conduit, said first conduit having a valve seat, stop means movably positioned in said second conduit for controlling the direction of flow of fluid from said second conduit to said first conduit, said stop means being normally maintained in said second conduit displaced from said first conduit to permit flow through said first conduit in said first direction, and said stop means being operable upon flow through said second conduit to move from said second conduit to said first conduit into sealing relation with said valve seat to block flow from said inlet to said outlet of said first conduit and direct flow from said second conduit to said first conduit and through said first conduit in a direction opposite to said first direction of flow through said first conduit.

2. In a gas analyzer, apparatus for developing a counterflow in a fluid conveying conduit as set forth in claim 1 which includes, said second conduit having an inlet for receiving fluid flow and an outlet communicating said first conduit between said inlet and said outlet of said first conduit, a seat within said second conduit between said inlet and said outlet of said second conduit for normally maintaining said stop means in said second conduit to permit flow through said first conduit in said first direction from said inlet to said outlet of said first conduit, said stop means being operable to move from said second conduit into sealing relation with said valve seat when the fluid pressure exerted upon said stop means by fluid flow through said second conduit is sufficient to move said stop means from said second conduit into said first conduit, and said stop means being retained in sealing relation with said valve seat by flow of fluid from said inlet to said outlet of said second conduit to thereby direct fluid flow through said first conduit in a direction opposite to said first direction.

3. In a gas analyzer, apparatus for developing a counterflow in a fluid conveying conduit as set forth in claim 1 which includes, said second conduit having an inlet for receiving fluid flow and an outlet connected to said first conduit between said inlet and said outlet of said first conduit, and guide means positioned in said first conduit and extending from said outlet of said second conduit to said valve seat for guiding movement of said stop means from said second conduit to said first conduit and into sealing relation with said valve seat when the fluid pressure on said stop means is sufficient to move said stop means from said second conduit into said first conduit.

4. In a gas analyzer, apparatus for developing a counterflow in a fluid conveying conduit as set forth in claim 3 which includes, said stop means being maintained in sealing relation with said valve seat of said first conduit by fluid flow from said inlet to said outlet of said second conduit, and said stop means being operable in sealing relation with said valve seat to block fluid flow to said first conduit outlet and direct fluid flow from said second conduit outlet to said first conduit inlet.

5. In a gas analyzer, apparatus for developing a counterflow in a fluid conveying conduit as set forth in claim 1 which includes, said stop means being operable upon a preselected decrease in the fluid flow from said inlet to said outlet of said second conduit to move out of sealing relation with said valve seat in said first conduit and into said second conduit and thereby permit fluid flow from said inlet to said outlet of said first conduit.

6. In a gas analyzer, apparatus for developing a counterflow in a fluid conveying conduit as set forth in claim 1 which includes, said second conduit having an inlet for receiving fluid flow and an outlet opening into said first conduit for directing fluid flow thereto, means for normally retaining said stop means in said second conduit between said inlet and outlet thereof, said valve seat in said first conduit being positioned oppositely of said second conduit outlet, said first conduit at said valve seat having an inside diameter of a dimension arranged to prevent movement of said stop means past said valve seat, a pin positioned within said first conduit, said pin being positioned at a location within said first conduit so that said stop means is moved toward said valve seat, and said stop means being operable to move from said second conduit into said first conduit and be deflected by said pin toward said valve seat so that the pressure exerted upon said stop means by the flow of fluid through said second conduit urges said stop means into sealing relation with said valve seat.

7. In a gas analyzer, apparatus for developing a counterflow in a fluid conveying conduit as set forth in claim 1 in which said stop means includes, a substantially spherical-shaped member arranged to move from second conduit into said first conduit and into sealing relation with said valve seat as determined by the fluid pressure exerted upon said spherical-shaped member by fluid flow in said first and second conduits.

8. In a gas analyzer, apparatus for developing a counterflow in a fluid conveying conduit as set forth in claim 1 which includes, a loop conduit having an inlet leg and outlet leg, said inlet and outlet legs being connected and positioned in spaced lateral relation to each other, said first conduit forming the end portion of said outlet leg, sensing means for analyzing the condition of a gas, said sensing means being connected to said outlet leg upstream of said first conduit and operable to receive a sample of the gas flowing normally in a direction from said inlet leg to said outlet leg, and said stop means being operable when the pressure of the fluid flowing through said second conduit is greater than the pressure of the gas flowing through said loop conduit to move from said second conduit to said first conduit and into sealing relation with said valve seat to direct fluid flow through said outlet leg and said inlet leg in a direction opposite to the normal direction of flow of the gas through said loop conduit.

9. In a gas analyzer, apparatus for developing a counterflow in a fluid conveying conduit as set forth in claim 1 which includes, valve means connected to said second conduit for controlling the flow of fluid under pressure from a source to said second conduit, and said valve means being operable to supply fluid under pressure to said second conduit to exert upon said stop means sufficient pressure to move said stop means from said second conduit to said first conduit and into sealing relation with said valve seat.

10. In a gas analzyer, apparatus for developing a counterflow in a fluid conveying conduit as set forth in claim 1 which includes, valve means connected to said second conduit for supplying a flow of fluid under pressure from a source to said second conduit, and said valve means being operable to supply fluid to said second conduit at a preselected pressure for moving said stop means to a position within said second conduit to permit fluid to flow through said second conduit into said first conduit and thereby prevent the fluid flowing through said first conduit in said first direction from entering said second conduit and contacting said stop means.

* * * * *